(12) United States Patent
Hyodo et al.

(10) Patent No.: US 8,895,632 B2
(45) Date of Patent: Nov. 25, 2014

(54) ANTHRACENE DERIVATIVE, COMPOUND OBTAINED THEREFROM, COMPOSITION, CURED PRODUCT, AND PROCESS FOR PRODUCING SAME

(75) Inventors: Hiroyuki Hyodo, Aichi (JP); Hidekazu Konishi, Aichi (JP)

(73) Assignee: Asahi Organic Chemicals Industry Co., Ltd., Miyazaki (JP)

( * ) Notice: Subject to any disclaimer, the term of this patent is extended or adjusted under 35 U.S.C. 154(b) by 295 days.

(21) Appl. No.: 13/502,736

(22) PCT Filed: Oct. 15, 2010

(86) PCT No.: PCT/JP2010/068165
§ 371 (c)(1),
(2), (4) Date: Jun. 4, 2012

(87) PCT Pub. No.: WO2011/049021
PCT Pub. Date: Apr. 28, 2011

(65) Prior Publication Data
US 2012/0232240 A1    Sep. 13, 2012

(30) Foreign Application Priority Data

Oct. 19, 2009   (JP) .................................. 2009-240370
Apr. 23, 2010   (JP) .................................. 2010-100406

(51) Int. Cl.
| | | |
|---|---|---|
| C07C 39/12 | (2006.01) | |
| C08G 59/68 | (2006.01) | |
| C07C 39/15 | (2006.01) | |
| C07C 39/14 | (2006.01) | |

(52) U.S. Cl.
CPC ................ C07C 39/14 (2013.01); C07C 39/15 (2013.01); C07C 2103/224 (2013.01)
USPC .............................. 518/718; 568/719; 528/94

(58) Field of Classification Search
CPC ...... C07C 2103/24; C07C 39/14; C07C 39/15
USPC ................................... 568/718, 719; 528/94
See application file for complete search history.

(56) References Cited

FOREIGN PATENT DOCUMENTS

| | | |
|---|---|---|
| CN | 101184732 | 5/2008 |
| JP | 04-282331 | 10/1992 |
| JP | 05-222153 | 8/1993 |
| JP | 06-295151 | 10/1994 |
| JP | 07-082221 | 3/1995 |
| JP | 09-328534 | 12/1997 |
| JP | 2003-064151 | 3/2003 |
| JP | 2005-346024 | 12/2005 |
| JP | 2007-099637 | 4/2007 |
| JP | 2008-001637 | 1/2008 |
| JP | 2009-040765 | 2/2009 |

OTHER PUBLICATIONS

International Search Report for International Application No. PCT/JP2010/068165, Dec. 7, 2010.

*Primary Examiner* — Jafar Parsa
(74) *Attorney, Agent, or Firm* — Ditthavong & Steiner, PC

(57) ABSTRACT

An object of the invention is to provide an anthracene derivative having characteristics peculiar to anthracene such as e.g., high carbon density, high melting point, high refractive index and fluorescent properties for ultraviolet rays, etc., and reaction diversity that results from the bisphenol structure, and a process for producing the same. Disclosed is an anthracene derivative represented by the following general formula (1):

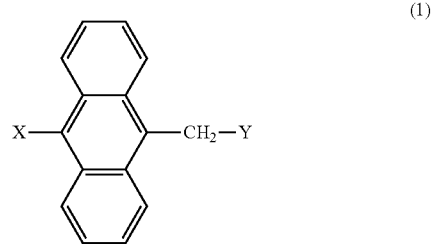

(1)

in the formula (1), X and Y each independently represent a hydroxyaryl group. The aforementioned X and Y are preferably a hydroxyphenyl group. In addition, the anthracene derivative can be produced by a process including allowing at least one compound selected from phenols and anthracene-9-carboaldehyde to react in the presence of an oxygen-containing inert organic solvent and an acid catalyst.

7 Claims, 16 Drawing Sheets

ANTHRACENE DERIVATIVE, COMPOUND OBTAINED THEREFROM, COMPOSITION, CURED PRODUCT, AND PROCESS FOR PRODUCING SAME

TECHNICAL FIELD

The present invention relates to a novel anthracene derivative, a compound obtained using the same as an intermediate, a composition containing the same and a cured product thereof, and a process for producing the anthracene derivative.

BACKGROUND ART

Conventionally, anthracene has been used in a variety of intended usages such as pesticides and storage stabilizers of wood, paints, etc., as well as basic materials for producing epoxy resins and carbon black, basic materials for synthesizing anthraquinone dyes, and the like.

In addition, since anthracene is a condensed polycyclic aromatic compound in which three benzene rings are condensed, it has characteristic features such as structural hardness, high carbon density, high melting point and high refractive index, as well as useful characteristics such as ability to emission of fluorescence by an action of π electron upon irradiation with ultraviolet rays, and the like. In an effort to more practically utilize such characteristics as additional values, a variety of developments of applications of anthracene have been attempted. So far, various anthracene derivatives have been developed as materials having high additional values in a large variety of technical fields.

For example, introduction of a (meth)acrylate group into 9, 10 positions of anthracene to give a polymerizable monomer enables a photocurable polymer that acts as a sensitizing agent of photoradical polymerization (see Japanese Unexamined Patent Application, Publication No. 2007-99637, etc.), as well as a polymer having ultraviolet ray absorptive capacity and flame retardance (see Japanese Unexamined Patent Application, Publication No. 2008-1637, etc.) to be obtained.

In addition, also in the field of photoresists, radiation sensitive resin compositions having advantages such as high sensitivity, high resolving ability, high etching resistance, low sublimability, etc., (see Japanese Unexamined Patent Application, Publication No. 2005-346024, etc.), as well as antireflection films capable of preventing intermixing with a resist resin (see Japanese Unexamined Patent Application, Publication No. H7-82221, etc.), and the like can be obtained using anthracene.

Moreover, applications of anthracene to intended usages for organic photo conductors (OPC), organic electroluminescent devices, organic solar cells, organic light emitting diodes and the like as materials for electron transport or luminescent materials (see Japanese Unexamined Patent Application, Publication No. 2009-40765, etc.).

In addition, taking advantages of a characteristic feature of having a high refractive index, anthracene has been used not only as optical materials, but also as hologram recording materials by mixing with a material having high refractive index, a material having low refractive index and a sensitizing pigment, etc., to permit recording of moire screen patterns upon exposure (see Japanese Unexamined Patent Application, Publication No. H6-295151, etc.).

On the other hand, with regard to bisphenol compounds having at least two aromatic rings, for example, bisphenolfluorene has been used for producing various types of novel polymers such as e.g., epoxy resins, polycarbonate resins, acrylate resins, arylic oligomers and the like, by means of reactivity of a hydroxyl group bound to the aromatic ring in the molecule, and/or the aromatic ring per se (for example, see Japanese Unexamined Patent Application, Publication No. H9-328534, etc.). Resins derived from these bisphenol compounds are employed in a variety of intended usages such as optical materials, electronic materials and the like. Accordingly, bisphenol compounds have particularly attracted attention due to having various reactivities, and versatility that allows for a large variety of developments of applications.

Therefore, development of a novel compound having an anthracene skeleton and a bisphenol structure that enables advanced functionalization of a material, and achievement of new characteristics has been desired.

PRIOR ART DOCUMENTS

[Patent Documents]
Patent Document 1: Japanese Unexamined Patent Application, Publication No. 2007-99637
Patent Document 2: Japanese Unexamined Patent Application, Publication No. 2008-1637
Patent Document 3: Japanese Unexamined Patent Application, Publication No. 2005-346024
Patent Document 4: Japanese Unexamined Patent Application, Publication No. H7-82221
Patent Document 5: Japanese Unexamined Patent Application, Publication No. 2009-40765
Patent Document 6: Japanese Unexamined Patent Application, Publication No. H6-295151
Patent Document 7: Japanese Unexamined Patent Application, Publication No. H9-328534

SUMMARY OF THE INVENTION

Problems to be Solved by the Invention

The present invention was made in view of the foregoing circumstances, and an object of the invention is to provide an anthracene derivative having characteristics peculiar to anthracene (i.e., high carbon density, high melting point, high refractive index, and fluorescent properties for ultraviolet rays, etc.), and reaction diversity that results from the bisphenol structure, and a process for producing the same.

Means for Solving the Problems

An aspect of the invention which was made in order to solve the aforementioned problems is an anthracene derivative represented by the following general formula (1):

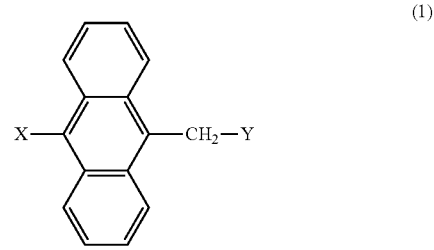

in the formula (1), X and Y each independently represent a hydroxyaryl group.

Due to having an anthracene skeleton, the anthracene derivative has various characteristics peculiar to anthracene such as e.g., high carbon density, high refractive index and fluorescent properties for ultraviolet rays, and has a melting point higher than anthracene due to substituents having an aromatic ring introduced at positions 9 and 10 of the anthracene skeleton.

In addition, the anthracene derivative has diversified reactivities provided by a bisphenol compound since two aforementioned substituents have a reactive hydroxyl group and an aromatic ring. Also, the anthracene derivative has, due to having an anthracene skeleton, a melting point and a refractive index comparative to or higher than those of bisphenol compounds such as bisphenolfluorene. Therefore, according to the anthracene derivative, superior versatility can be achieved which includes usability for various types of basic materials of resins and the like.

It is preferred that in the anthracene derivative described above, the X and Y be a hydroxyphenyl group. Such an anthracene derivative can achieve, in particular, a high melting point and refractive index, and can be efficiently produced.

Moreover, a compound obtained using the anthracene derivative as an intermediate material can have additional peculiar properties provided by introducing each functional group, thereby enabling use as a basic material of resins for synthesizing various resins.

Therefore, a composition containing the anthracene derivative or the compound obtained using the anthracene derivative as an intermediate can be used as a basic material of a resin composition for synthesizing various resins having superior versatility and additional values, and the like. Also, a cured product obtained by curing the composition can be provided with a high refractive index, high melting point, fluorescent properties and the like due to having an anthracene skeleton, thereby allowing for use as a resin applicable in many fields.

Another aspect of the present invention which was made for solving the aforementioned problems is a process for producing an anthracene derivative represented by the following formula (1), the process including allowing at least one compound selected from phenols to react with anthracene-9-carboaldehyde in the presence of an oxygen-containing inert organic solvent and an acid catalyst.

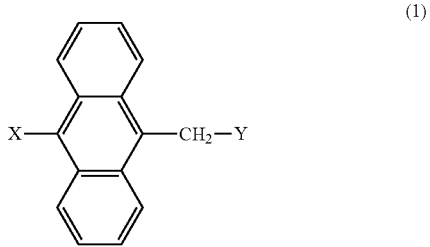

(1)

in the formula (1), X and Y each independently represent a hydroxyaryl group.

According to the process for the production, occurrence of a side reaction can be inhibited, and the anthracene derivative desired can be more efficiently produced by selecting the type of the phenols. For example, when phenol is selected among the phenols, an anthracene derivative in which X and Y in the above formula (1) are both a hydroxyphenyl group can be produced.

Effects of the Invention

As explained in the foregoing, the anthracene derivative of the present invention has a high melting point comparative to or higher than those of anthracene and bisphenol compounds, and also has various characteristics peculiar to anthracene such as e.g., high carbon density, high refractive index and fluorescent properties for ultraviolet rays, and the like. Still further, the anthracene derivative not only has various characteristics peculiar to anthracene but exhibits diversified reactivities provided by a bisphenol compound; therefore, achieving superior versatility such as a possibility of use for various types of basic materials of resins, etc., is enabled.

Therefore, the anthracene derivative of the present invention, the compound obtained using the anthracene derivative as an intermediate, a composition containing the same and a cured product are extremely effective in advanced functionalization of a material, and achievement of new characteristics, thereby enabling development of applications in a large variety of technical fields to be aimed therewith as basic materials of resins having superior versatility and additional values such as e.g., basic materials of epoxy resins, basic materials of polycarbonate resins, basic materials of acrylic resins, laminating materials, coating materials such as paints, optical materials such as lenses and optical sheets, recording materials such as hologram recording materials, advanced functional materials such as organic photo conductors, photoresist materials, antireflection films and semiconductor sealing materials, magnetic materials such as magnetic molecular memory, organic solar cells, organic EL devices, and the like.

Additionally, according to the process for the production of the present invention, the anthracene derivative desired can be efficiently produced.

DESCRIPTION OF EMBODIMENTS

Figure 1:
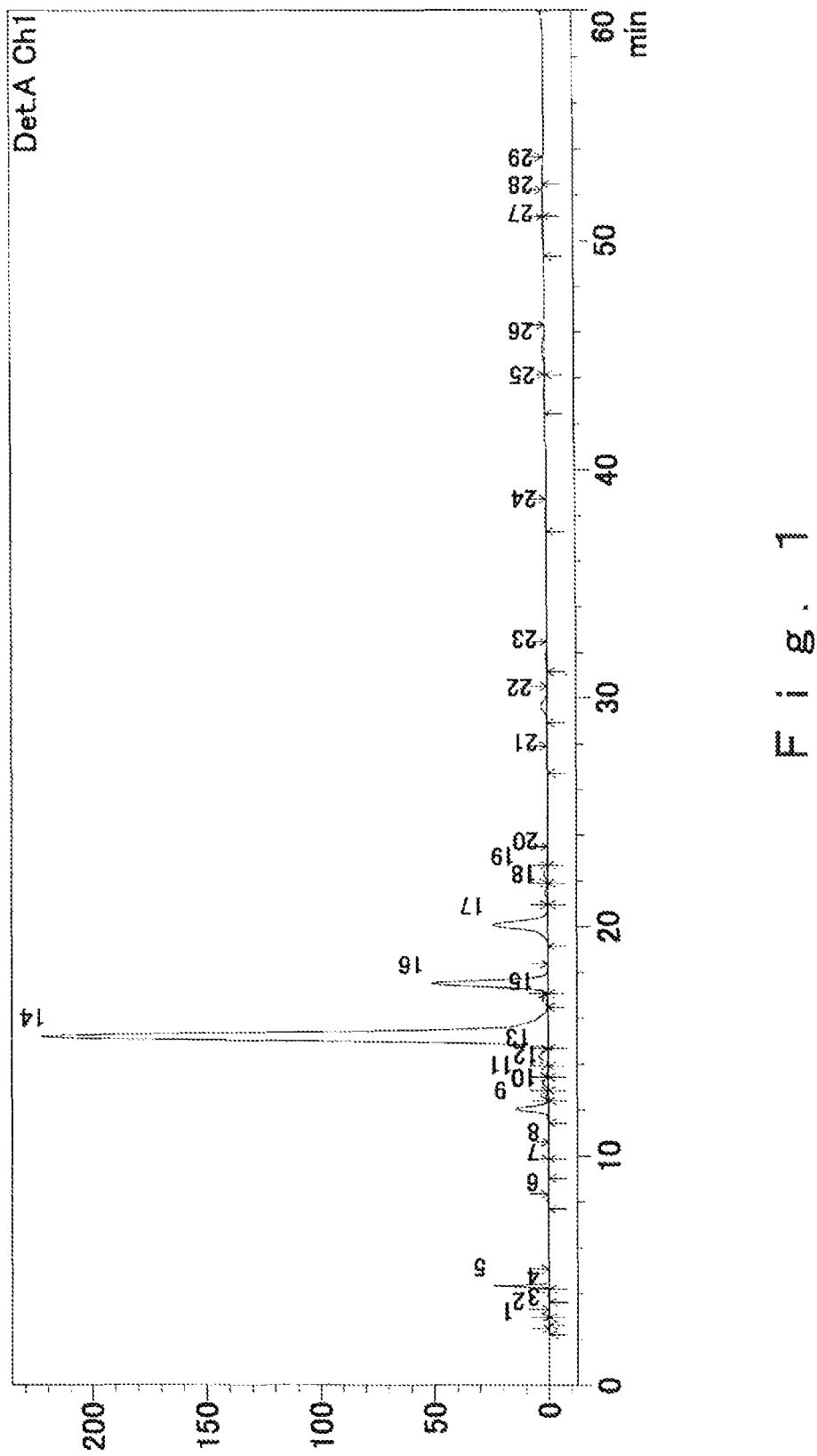
FIG. 1 shows a view illustrating an HPLC chart obtained after completing the reaction of Example 1.

Hereinafter, embodiments of the present invention are explained in detail in the order of the anthracene derivative, the compound and the like obtained using the same, and the process for the production thereof.

<Anthracene Derivative>

The anthracene derivative of the present invention is represented by the above general formula (1).

Due to having an anthracene skeleton, the anthracene derivative has a high carbon density, a high refractive index and fluorescent properties for ultraviolet rays, which have various characteristics peculiar to anthracene, and has a melting point higher than anthracene due to substituents having an aromatic ring (i.e., a hydroxyaryl group) introduced at positions 9 and 10 of the anthracene skeleton.

The anthracene derivative not only has various characteristics peculiar to anthracene, but also has diversified reactivities provided by a bisphenol compound since the two hydroxyaryl groups further have a reactive hydroxyl group and an aromatic ring. For example, the anthracene derivative may be subjected to allylation, glycidylation, acrylation, methylolation, benzooxazination.

Moreover, the anthracene derivative has a high melting point and a high refractive index comparative to or higher than those of bisphenol compounds such as bisphenolfluorene, due to having an anthracene skeleton. Specifically, the anthracene derivative has a melting point of no less than 218° C. and no greater than 300° C., and a refractive index of no less than 1.6 and no greater than 2.0. The melting point and the refractive index of the anthracene derivative may be adjusted by appropriately selecting the substituents represented by X and Y.

Therefore, according to the anthracene derivative, superior versatility can be achieved which includes usability for various types of basic materials of resins and the like. Particularly, since the phenol skeleton is placed at positions 9 and 10 of the anthracene ring, the anthracene derivative has superior symmetry, and favorable development of applications in enabled such as introduction into the polymer main chain permitted when used as a basic material of a resin, and the like. Particularly, the anthracene derivative has phenol skeletons placed at positions 9 and 10 to correspond to short axis of the anthracene skeleton; therefore, when introduced into the polymer main chain, achievement of peculiar functions is expected such as attaining extremely high carbon density of the polymer, or giving high crystallinity.

The hydroxyaryl group is a substituent that has at least one hydroxy group, and is accompanied by elimination of one hydrogen atom from an aromatic ring of the aromatic hydrocarbon which may have other substituent. Specific examples of the hydroxyaryl group include a hydroxyphenyl group, a hydroxynaphthyl group and the like, and those obtained by substituting a hydrogen atom on these aromatic rings with a substituent such as an alkyl group, a hydroxy group, an alkoxyl group, an aryl group, an alkenyl group, an amino group or a mercapto group. It is to be noted that a plurality of substituents may be present on the aromatic ring.

Examples of the alkyl group include linear, branched, monocyclic or condensed polycyclic alkyl groups, or linear, branched, monocyclic or condensed polycyclic alkyl groups in which carbon is substituted with —O—, and the like. Specific examples of the linear, branched, monocyclic or condensed polycyclic alkyl group include a methyl group, an ethyl group, a propyl group, a butyl group, a pentyl group, a hexyl group, a heptyl group, an octyl group, a nonyl group, a decyl group, a dodecyl group, an octadecyl group, an isopropyl group, an isobutyl group, an isopentyl group, a sec-butyl group, a tert-butyl group, a sec-pentyl group, a tert-pentyl group, a tert-octyl group, a neopentyl group, a cyclopropyl group, a cyclobutyl group, a cyclopentyl group, a cyclohexyl group, an adamantyl group, a norbornyl group, a boronyl group, a 4-decylcyclohexyl group, and the like. Moreover, specific examples of the linear, branched chain alkyl group interrupted by at least one —O— include —$CH_2$—O—$CH_2$, —$CH_2$—$CH_2$—O—$CH_2$—$CH_2$, —$CH_2$—$CH_2$—$CH_2$—O—$CH_2$—$CH_2$, —$(CH_2$—$CH_2$—O$)_{n1}$—$CH_3$ (wherein, n1 is an integer of 1 to 8), —$(CH_2$—$CH_2$—$CH_2$—O$)_{m1}$—$CH_2$ (wherein, m1 is an integer of 1 to 5), —$CH_2$—CH($CH_2$)—O—$CH_2$—$CH_2$, —$CH_2$—CH(O$CH_3)_2$, and the like.

Examples of the alkoxyl group include linear, branched, monocyclic or condensed polycyclic alkoxyl groups, or linear, branched, monocyclic or condensed polycyclic alkoxyl groups interrupted by at least one —O—, and the like. Specific examples of the linear, branched, monocyclic or condensed polycyclic alkoxyl group include a methoxy group, an ethoxy group, a propoxy group, a butoxy group, a pentyloxy group, a hexyloxy group, a heptyloxy group, an octyloxy group, a nonyloxy group, a decyloxy group, a dodecyloxy group, an octadecyloxy group, an isopropoxy group, an isobutoxy group, an isopentyloxy group, a sec-butoxy group, a tert-butoxy group, a sec-pentyloxy group, a tert-pentyloxy group, a tert-octyloxy group, a neopentyloxy group, a cyclopropyloxy group, a cyclobutyloxy group, a cyclopentyloxy group, a cyclohexyloxy group, an adamantyloxy group, a norbornyloxy group, a boronyloxy group, a 4-decylcyclohexyloxy group, and the like. Also, specific examples of the linear, branched chain alkoxyl group interrupted by at least one —O— include —O—$CH_2$—O—$CH_3$, —O—$CH_2$—$CH_2$—O—$CH_2$—$CH_2$, —O—$CH_2$—$CH_2$—$CH_2$—O—$CH_2$—$CH_2$, —O—$(CH_2$—$CH_2$—O$)_{n2}$—$CH_3$ (wherein, n2 is an integer of 1 to 8), —O—$(CH_2$—$CH_2$—$CH_2$—O$)_{m2}$—$CH_3$ (wherein, m2 is an integer of 1 to 5), —O—$CH_2$—CH($CH_3$)—O—$CH_2$—$CH_3$, —O—$CH_2$—CH(O$CH_3)_2$, and the like.

Examples of the aryl group include groups obtained by eliminating one hydrogen atom from an aromatic ring which may have a substituent, and specific examples include a phenyl group, a 1-naphthyl group, a 2-naphthyl group, a 1-anthryl group, a 9-anthryl group, a 2-phenanthryl group, a 3-phenanthryl group, a 9-phenanthryl group, a 1-pyrenyl group, a 5-naphthacenyl group, a 1-indenyl group, a 2-azulenyl group, a 1-acenaphthyl group, a 2-fluorenyl group, a 9-fluorenyl group, a 3-perylenyl group, an o-tolyl group, a m-tolyl group, a p-tolyl group, a 2,3-xylyl group, a 2,5-xylyl group, a mesityl group, a p-cumenyl group, a p-dodecylphenyl group, an o-methoxyphenyl group, a m-methoxyphenyl group, a p-methoxyphenyl group, a 2,6-dimethoxyphenyl group, a 3,4-dimethoxyphenyl group, a 3,4,5-trimethoxyphenyl group, a p-cyclohexylphenyl group, a 4-biphenyl group, an o-fluorophenyl group, a m-chlorophenyl group, a p-bromophenyl group, a p-hydroxyphenyl group, a m-carboxyphenyl group, an o-mercaptophenyl group, a p-cyanophenyl group, a m-nitrophenyl group, a m-azidophenyl group, and the like.

Examples of the alkenyl group include linear, branched, monocyclic or condensed polycyclic alkenyl groups and the like, which may have a plurality of carbon-carbon double bonds in their structures, and specific examples are a vinyl group, a 1-propenyl group, an allyl group, a 2-butenyl group, a 3-butenyl group, an isopropenyl group, an isobutenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, a cyclopentenyl group, cyclohexenyl group, a 1,3-butadienyl group, a cyclohexadienyl group, a cyclopentadienyl group, and the like.

Anthracene derivatives provided with a hydroxyaryl group having a substituent exemplified as the hydroxyaryl group can further add or adjust the function while maintaining the characteristic features of the anthracene derivative.

For example, the anthracene derivative provided with a hydroxyaryl group having an alkyl group as a substituent can adjust the refractive index and the melting point without deteriorating diversified reactivities of the anthracene derivative. It is to be noted that the substituted alkyl group preferably has a low molecular weight in light of configurational stability of the anthracene derivative, and specifically, an alkyl group having no greater than 5 carbon atoms is preferred, and a methyl group or an ethyl group is particularly preferred.

In addition, according to the anthracene derivative provided with a hydroxyphenyl group or hydroxynaphthyl group having at least two hydroxy groups, further development of applications is enabled as, for example, crosslinking reactivities are improved since a plurality of hydroxy groups are present on one aromatic ring.

Among the hydroxyaryl groups, in light of superior refraction properties, high melting point and reaction diversity, unsubstituted hydroxyphenyl groups and unsubstituted hydroxynaphthyl groups are preferred, unsubstituted hydroxyphenyl groups are particularly preferred, and a 4-hydroxyphenyl group is most preferred. Furthermore, X and Y may be different, but are preferably the same in light of superior refraction properties, ease in production, and the like.

Due to having the above structure, the anthracene derivative of the present invention can be used as various types of basic materials of synthetic resins such as basic materials of epoxy resins, basic materials of polycarbonate resins and basic materials of acrylic resins by introducing directly or as a reaction intermediate. Moreover, the anthracene derivative can be used as, in addition to basic materials of synthetic resins, for example, intermediates of pesticides and intermediates of medicines.

<Compound Obtained Using Anthracene Derivative as an Intermediate>

The compound obtained using the anthracene derivative as an intermediate may be obtained by subjecting the anthracene derivative to allylation, glycidylation (for example, 9-(4-hydroxybenzyl)-10-(4-hydroxyphenyl) anthracene diglycidyl ether, etc.), acrylation, methylolation, benzooxazination or the like. These compounds can be used as basic materials of resins such as basic materials of epoxy resins and basic materials of acrylic resins. Since these compounds obtained using the anthracene derivative as an intermediate also has an anthracene skeleton, they have properties peculiar to anthracene such as a high melting point, high refractive index, and fluorescent properties. Therefore, the resin obtained with the compound can also have further additional values, i.e., having a high refractive index and functions such as fluorescent properties, and the like.

<Composition>

The anthracene derivative, or the composition containing the compound obtained using the anthracene derivative as an intermediate can be used for basic materials of resins such as basic materials of epoxy resins, basic materials of polycarbonate resins and basic materials of acrylic resins, as well as adhesives, paints and the like. Other components in the composition may include well-known components used in producing each resin. The other components may include a solvent, an inorganic filler, a pigment, a thixotropifying agent, a flow performance improver, other monomer, and the like.

Although the solvent may vary depending on the constitution of the composition, for example, ethers, diethylene glycol alkyl ethers, ethylene glycol alkyl ether acetates, propylene glycol monoalkyl ethers, propylene glycol monoalkyl ether acetates, propylene glycol monoalkyl ether propionates, aromatic hydrocarbons, ketones, esters, and the like may be exemplified.

Further, the inorganic filler is exemplified by silica powder such as spherical or crashed molten silica, or crystal silica, alumina powder, glass powder, mica, talc, calcium carbonate, alumina, hydrated alumina, and the like. The pigment is exemplified by organic or inorganic extender pigments, scale-like pigments, and the like. The thixotropifying agent is exemplified by silicon based, castor oil based and aliphatic amide waxes, as well as polyethylene oxide waxes and organic bentonite based waxes, and the flow performance improver is exemplified by phenyl glycidyl ether, naphthyl glycidyl ether, and the like.

<Cured Product>

Moreover, the cured product obtained by curing the composition can be used as various types of resins. Also, these cured products may be used in various intended usage as a highly versatile material that imparts various characteristics such as a high melting point, high refractive index, and fluorescent properties derived from the anthracene skeleton. It is to be noted that the cured product can be obtained by subjecting the composition to a well-known method that is appropriate for each composition, such as irradiation with light or heating.

These cured products may be used as various types of synthetic resins such as epoxy resins, polycarbonate resins and acrylic resins, and further, taking advantages of the functionality, these cured products may be used as optical materials such as lenses and optical sheets, recording materials such as hologram recording materials, advanced functional materials such as organic photo conductors, photoresist materials, antireflection films and semiconductor semiconductor encapsulation materials, and the like.

<Process for Producing Anthracene Derivative>

The anthracene derivative of the present invention is produced by a process including the step of allowing at least one compound selected from phenols to react with anthracene-9-carboaldehyde in the presence of an oxygen-containing inert organic solvent and an acid catalyst. Although the mechanism of the reaction is not certain, it is believed that the oxygen-containing inert organic solvent allows electrons on specific carbon of anthracene-9-carboaldehyde to be localized, and thus a reaction with the phenols is caused.

The phenols as referred to, mean compounds having a hydroxy group on the aromatic ring, and may include phenol compounds, naphthol compounds, and the like. The phenol compound as referred to, means phenol, and phenol having substitution of hydrogen on the aromatic ring with other substituent. The substituent is exemplified by an alkyl group a hydroxy group, and the like. The number of the substituent is, in light of the reactivity with anthracene-9-carboaldehyde, preferably no greater than 4, more preferably no greater than 2, and particularly preferably 0. In addition, in light of the reactivity with anthracene-9-carboaldehyde, it is preferred that any substituent of a hydroxy group is not present at the para-position.

Examples of the phenol compound include phenol, o-cresol, m-cresol, p-cresol, 2,3-xylenol, 2,4-xylenol, 2,5-xylenol, 2,6-xylenol, 3,4-xylenol, 3,5-xylenol, 2,3,5-trimethyl phenol, 2,3,6-trimethyl phenol, 2-ethyl phenol, 4-ethyl phenol, 2-isopropyl phenol, 4-isopropyl phenol, 2-tert-butyl phenol, 4-tert-butyl phenol, 2-cyclohexyl phenol, 4-cyclohexyl phenol, 2-phenyl phenol, 4-phenyl phenol, thymol, 2-tert-butyl-5-methyl phenol, 2-cyclohexyl-5-methyl phenol, resorcin, 2-methylresorcin, catechol, 4-methylcatechol, hydroquinone, pyrogallol, and the like.

The naphthol compound as referred to, means naphthol, and naphthol having substitution of hydrogen on the aromatic ring with other substituent. The substituent is exemplified by an alkyl group, a hydroxy group, and the like. In light of reactivity with anthracene-9-carboaldehyde, the number of the substituent is preferably no greater than 6, more preferably no greater than 2, and particularly preferably 0.

Examples of the naphthol compound include 1-naphthol, 2-naphthol, 1,4-dihydroxynaphthalene, 1,5-dihydroxynaphthalene, 1,6-dihydroxynaphthalene, 2,3-dihydroxynaphthalene, 2,6-dihydroxynaphthalene, 2,7-dihydroxynaphthalene, and the like.

The phenols are not particularly limit to the foregoings, and may be selected ad libitum depending on the structure of the anthracene derivative desired. For example, when phenol is selected among the phenols, an anthracene derivative in which X and Y in the above formula (1) are a hydroxyphenyl group may be produced. It is to be noted that these may be used either alone, or in combination of two or more thereof.

Furthermore, the lower limit of the amount of the phenols blended is, with respect to 1 mol of anthracene-9-carboaldehyde, preferably 2 mol, and more preferably 4 mol. The upper limit of the amount of the phenols blended is, with respect to 1 mol of anthracene-9-carboaldehyde, preferably 100 mol, more preferably 50 mol, and particularly preferably 20 mol. When the amount of the phenols blended is less than the aforementioned lower limit, higher-order condensates of the basic material are generated; therefore, a great deal of energy is required for purification. To the contrary, when the amount exceeds the aforementioned upper limit, a great deal of energy is required for eliminating unreacted phenols. Thus, the amount of the phenols out of the above range leads to economical disadvantages.

In the process for the production, an oxygen-containing inert organic solvent having at least one oxygen atom in the molecule is used as a reaction solvent. The term "inert" as referred to, means to be unreactive with the phenols, anthracene-9-carboaldehyde and the anthracene derivative synthesized in the reaction system. Examples of the inert oxygen-containing organic solvent which may be used include alcohols, polyhydric alcohol ethers, cyclic ethers, polyhydric alcohol esters, ketones, esters, sulfoxides, carboxylic acids, and the like.

Examples of the alcohols include monovalent alcohols such as methanol, ethanol, propanol and butanol, bivalent alcohols such as butanediol, pentanediol, hexanediol, ethylene glycol, propylene glycol, trimethylene glycol, diethylene glycol, dipropylene glycol, triethylene glycol, tripropylene glycol and polyethylene glycol, trivalent alcohols such as glycerin, and the like.

Examples of the polyhydric alcohol ether include glycol ethers such as ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethylmethyl ether, and ethylene glycol monophenyl ether.

Examples of the cyclic ethers include 1,3-dioxane, 1,4-dioxane, tetrahydrofuran, and the like. Examples of the polyhydric alcohol ester include glycol esters such as ethylene glycol acetate. Examples of the ketones include acetone, methyl ethyl ketone, and the like. Examples of the esters include ethyl acetate, propyl acetate, butyl acetate, and the like. Examples of the sulfoxides include dimethyl sulfoxide, diethyl sulfoxide, and the like. Examples of the carboxylic acids include acetic acid, acetic anhydride, and the like.

Among these, alcohols and polyhydric alcohol ether are preferred, and methanol, ethylene glycol and ethylene glycol monomethyl ether are particularly preferred.

The oxygen-containing inert organic solvent is not limited to the above illustrative examples, and those may be each used wither alone, or as a mixture of two or more thereof. The lower limit of the amount of the oxygen-containing inert organic solvent blended is preferably 1 part by mass, more preferably 5 parts by mass, and particularly preferably 10 parts by mass with respect to 100 parts by mass of the phenols. In addition, the upper limit of the amount of the oxygen-containing inert organic solvent blended is preferably 1,000 parts by mass, more preferably 500 parts by mass, and particularly preferably 10 parts by mass with respect to 100 parts by mass of the phenols. When the amount of the oxygen-containing inert organic solvent blended is less than the aforementioned lower limit, production of by-products of the reaction may be remarkable, whereby productivity may be deteriorated. To the contrary, when the amount of the oxygen-containing inert organic solvent blended is beyond the aforementioned upper limit, the reaction rate is reduced, whereby the productivity may be deteriorated.

The acid catalyst in the present invention may be exemplified by inorganic acids such as hydrochloric acid, sulfuric acid, phosphoric acid and perchloric acid, organic acids such as oxalic acid, paratoluenesulfonic acid, methanesulfonic acid and phenolsulfonic acid, strong acids of resin acids such as strongly acidic ion exchange resins. These catalysts may be used either alone or in combination of two or more thereof, or may be used in combination with a catalytic promoter of the reaction such as mercaptoacetic acid. The amount of the acid catalyst used may be determined in the range so as to avoid the risk resulting from an extreme reaction but to be not too low for promoting the reaction, and in general, the amount of the acid catalyst may be 0.1 to 20% by mass with respect to the mass of the phenols.

The anthracene derivative may be produced by charging the phenols, anthracene-9-carboaldehyde, the oxygen-containing inert organic solvent and the acid catalyst in a reaction vessel, and stirring the mixture for a predetermined period of time. It is to be noted that the materials may be charged in any order into the reaction vessel.

The reaction temperature in the reaction step of the process for the production falls within the range of usually 0 to 100° C., and preferably 25 to 60° C. When the reaction temperature is too low, the reaction time may be too long, and to the contrary, when the reaction temperature is too high, purity of the anthracene derivative may be lowered since production of by-products of the reaction such as higher-order condensates and isomers is enhanced.

Although the pressure in the reaction vessel in the reaction step of the process for the production is usually ordinary pressure, the reaction may be carried out under compression or in vacuum. Specifically, the internal pressure (gauge pressure) preferably falls within the range of −0.02 to 0.2 MPa.

The reaction time in the reaction step of the process for the production may vary depending on the type, the amount and the molar ratio of the phenols and the oxygen-containing inert organic solvent used, as well as the reaction temperature, the pressure and the like, and cannot be decided categorically; however, in general, the reaction time preferably falls within the range of 1 to 48 hrs.

After completing the reaction of the process for the production, the acid catalyst is eliminated. In a method for eliminating the catalyst, in general, the product is dissolved in a water insoluble organic solvent such as methyl ethyl ketone or methyl isobutyl ketone, and then the acid catalyst is eliminated by washing with water; however, alternatively, a method in which a neutralizing treatment is carried out and thereafter thus deposited neutralized salt is filtered off, a method in which a resin acid such as anion exchange resin is directly filtered off, a method in which the reaction mixture is passed through a column packed with an anion filler, or the like may be employed but not particularly limited thereto.

In the process for the production, after removing the catalyst, the anthracene derivative is removed by purification. In general, the anthracene derivative that is an intended substance can be obtained by a method including adding an organic solvent that serves as a poor solvent for the intended substance but serves as a good solvent for other by-products and unreacted basic materials to permit precipitation, followed by filtering off the precipitates and drying.

EXAMPLES

Next, the present invention is explained in more detail by way of Examples, but the present invention is not any how limited to these Examples. It is to be noted that with respect to the resulting anthracene derivative, the compound obtained using the anthracene derivative as an intermediate, and the cured product, determination was carried out with the following instruments and methods for determination.

<Purity on GPC>

The purity on GPC was determined using GPC, model HLC-8220, an RI detector, and TSK-Gel Super HZ2000+HZ1000+HZ1000 (4.6 mmϕ×150 mm) columns manufactured by Tosoh Corporation, with feeding a liquid tetrahydrofuran as a developing solvent at a flow rate of 0.35 ml/min, and the determination was made based on the area ratio of the peak of the intended substance.

<Purity on HPLC>

The purity on HPLC and completion of the reaction were determined using HPLC Prominece series and a UV detector SPD-20A (246 nm) manufactured by Shimadzu Corporation, and ODS-3 (4.6 mmϕ×250 mm) column manufactured by GL Science, with feeding a liquid with feeding a liquid with feeding a liquid with feeding a liquid water/acetonitrile=40/60 as a developing solvent at a flow rate of 1.0 ml/min, and the determination was made based on the area ratio of the peak of the intended substance.

<Melting Point and Glass Transition Temperature (Tg)>

The melting point was determined according to a peak top method using a differential scanning calorimeter, model DSC8230 manufactured by Rigaku Corporation in a nitrogen atmosphere at a rate of temperature rise of 5° C./min. In addition, the glass transition temperature was measured under similar conditions to determine a midpoint glass transition temperature.

<Coefficient of Linear Expansion>

The linear expansion coefficient was measured for confirming dimension accuracy. More specifically, the cured product was cut to give a test piece of 2.5 mm×3.0 mm×15.0 mm, and the length of the test piece was measured in an air atmosphere at a rate of temperature rise of 5° C./min up to 300° C. with a thermomechanical analyzer, model TMA8141BS manufactured by Rigaku Corporation to determine an average coefficient of thermal expansion (ppm/° C.) in the range of 30° C. to 280° C.

<Water Absorbing Rate>

The water absorbing rate was determined by cutting the cured product to give a test piece of 10 mm×10 mm×2.5 mm, and measuring the increase in mass (% by mass) after boiling in hot water for 8 hrs.

<Residual Carbon Ratio>

It is reported that a residual carbon ratio bears a proportionate relationship to an oxygen index, and in general, a resin having superior flame retardance has a high residual carbon ratio (see Document 1 below). With reference to this document, the residual carbon ratio was determined as a marker of flame retardance. In the determination method, a scale for differential scanning calorimetry manufactured by Rigaku Corporation, model TG8230 was used for the measurement in a nitrogen atmosphere at a rate of temperature rise of 10° C./min up to 830° C., and the residual carbon ratio was determined in terms of a value derived by subtracting the proportion of decrease in the mass (%) from 100%.

Document 1: It was verified that there is a linear relationship between a Krevelen oxygen index and the degree of carbonization of a polymer (Char Residue); D. W. van Krevelen, Polymer, 16, p 615 (1975) D. W. van Krevelen, Chimia, 28, p 504 (1974).

<$^1$H-NMR and $^{13}$C-NMR>

$^1$H-NMR and $^{13}$C-NMR were determined using UNITY-INOVA, 400 MHz manufactured by Varian Inc., with TMS of as a standard substance in a solvent of DMSO-d6.

<Refractive Index>

The refractive index was determined by dissolving the sample to give each concentration of 1% by mass, 5% by mass and 10% by mass in propylene glycol monomethyl ether acetate (PGMEA) and measuring using a refractometer, model RA-520N manufactured by Kyoto Electronics Manufacturing Co., Ltd., at 25° C., and producing a calibration curve to derive a converted refractive index at 100% by mass.

<Absorption Spectrum and Fluorescent Spectrum>

The absorption spectrum was determined by dissolving the sample in DMSO to give a concentration of $1 \times 10^{-5}$ mol/L and measuring using a spectrophotometer V-570 manufactured by JASCO Corporation. The fluorescent spectrum was determined by dissolving in DMSO to give concentration of $1 \times 10^{5\ mol}$/L, and measuring with excitation at a maximum wavelength using a fluorescent spectrophotometer F-4010 manufactured by Hitachi High-Technologies Corporation. In addition, the presence/absence of luminescence was observed using a handy UV lamp SLUV-4 manufactured by AS ONE Corporation while irradiating with an ultraviolet ray of 365 nm.

Example 1

In a 300 ml reaction vessel equipped with a reflux tube were charged 112.8 g (1.20 mol) of phenol, 49.4 g (0.24 mol) of anthracene-9-carboaldehyde and 11.3 g of methanol, and dissolution was permitted at 40° C. Thereto was charged 5.6 g of conc. sulfuric acid, and the reaction was allowed at 40° C. for 24 hrs. Then, disappearance of the peak of anthracene-9-carboaldehyde, and predominant production of the intended substance were ascertained on HPLC. An HPLC chart obtained after completing the reaction is shown in FIG. 1. Subsequently, the reaction mixture was dissolved in methyl isobutyl ketone (169.2 g) was dissolved in 56.4 g of distilled water, followed by washing with water several times to eliminate the catalyst. After methyl isobutyl ketone and phenol were distilled off under a reduced pressure, 169.2 g of xylene and 11.3 g of distilled water were charged and the mixture was stirred at 10° C. The crystal thus precipitated was filtered off, and thereafter dried under reduced pressure to obtain 48.3 g of pale yellow crystal (yield: 53.3%).

Figure 2:
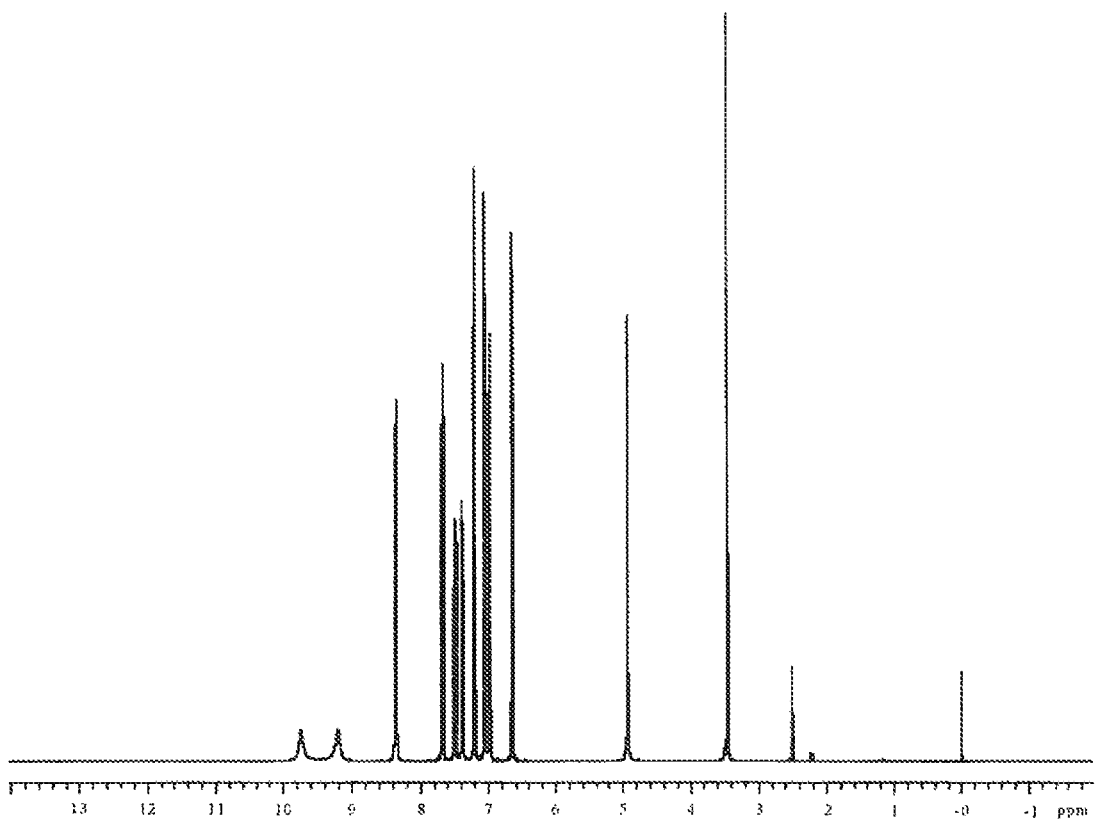
FIG. 2 shows a view illustrating a $^1$H-NMR chart of an intended product of Example 1.
Figure 3:
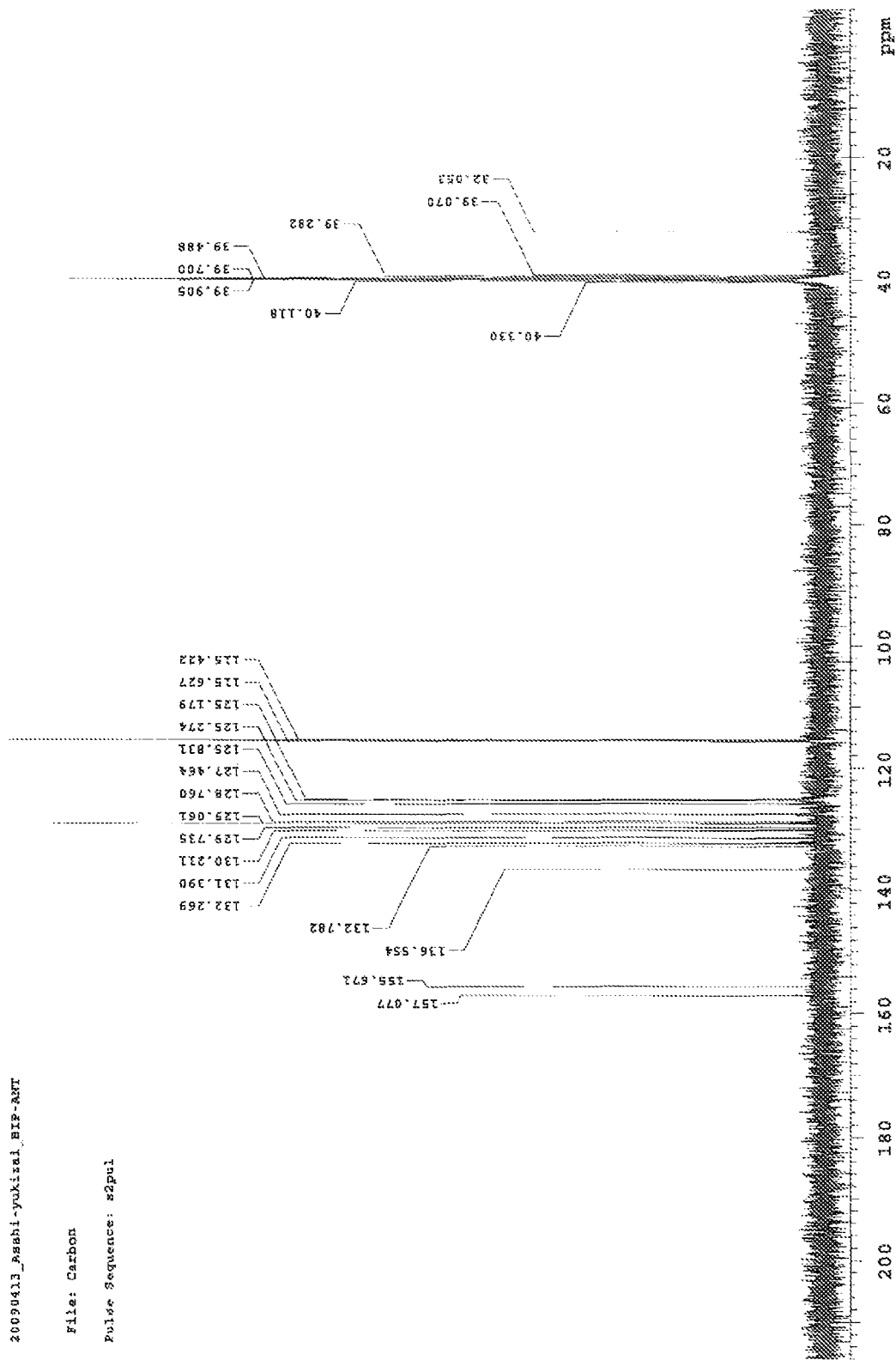
FIG. 3 shows a view illustrating a $^{13}$C-NMR chart of the intended product of Example 1.
Figure 4:
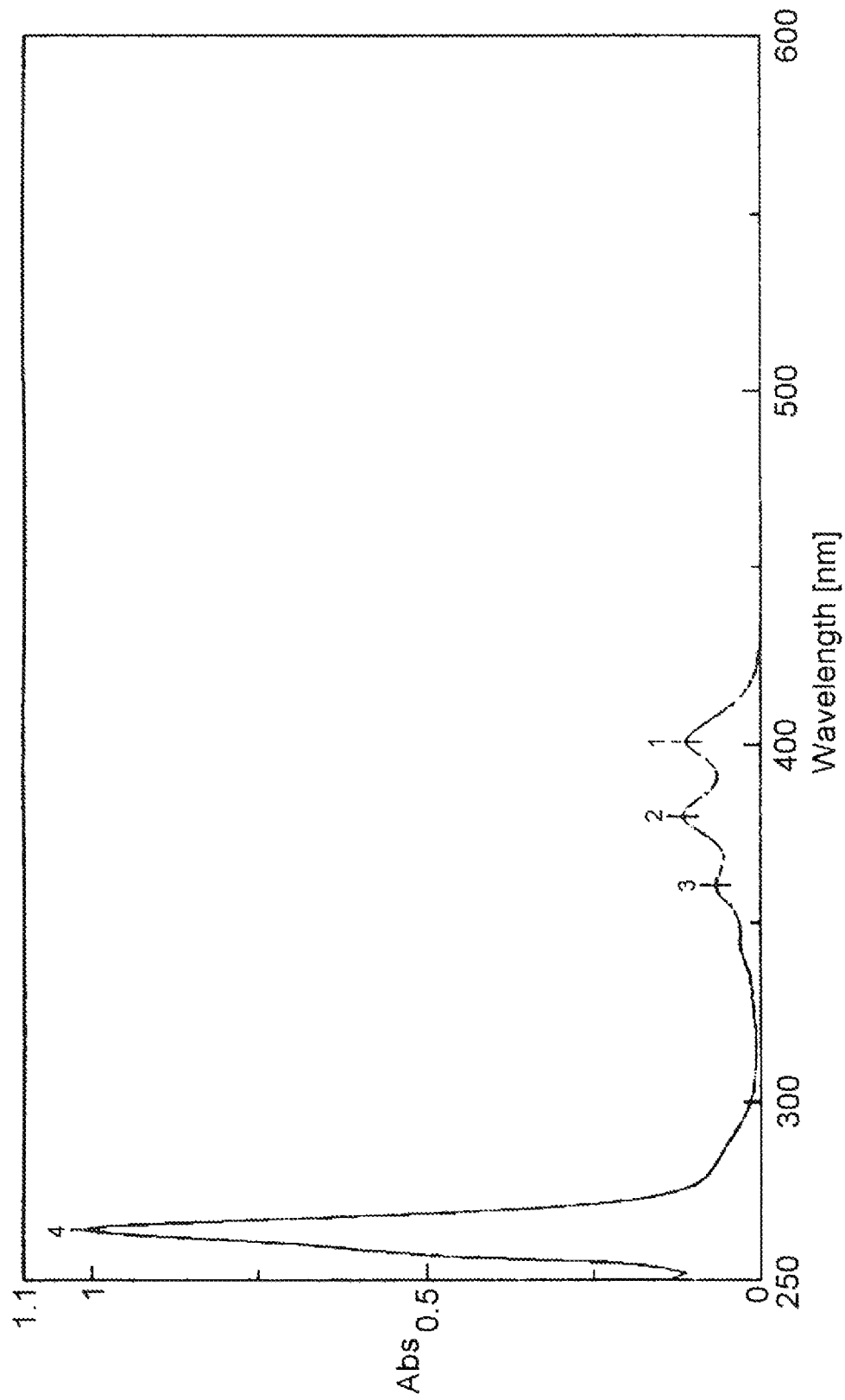
FIG. 4 shows a view illustrating an absorption spectrum of the intended product of Example 1.
Figure 5:
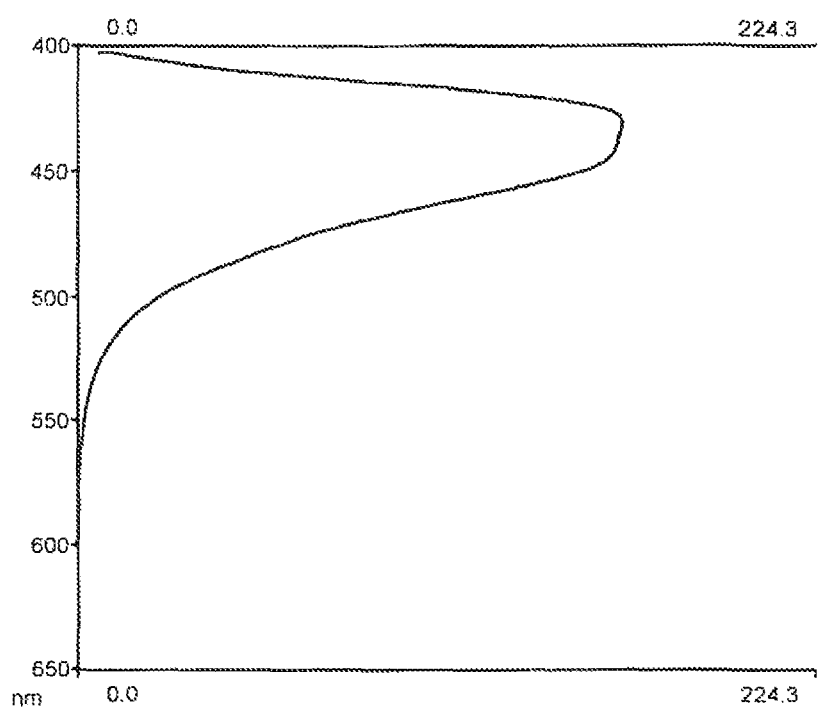
FIG. 5 shows a view illustrating a fluorescent spectrum of the intended product of Example 1.

The crystal obtained had a purity on GPC of 100%, a purity on HPLC of 99.4%, a melting point of 238° C. and a converted refractive index of 1.701 (25° C.), and ascertained to be 9-(4-hydroxybenzyl)-10-(4-hydroxyphenyl)anthracene by way of $^1$H-NMR (400 MHz, DMSO-d6, δ, ppm/4.9, 2H, —C$\underline{H_2}$—/6.6, 6.9, 7.1, 7.2, 8H, Phenyl-$\underline{H}$/7.3, 7.5, 7.7, 8.4, 8H, Anthryl-$\underline{H}$/9.2, 9.8, 2H, —O$\underline{H}$) and $^{13}$C-NMR (400 MHz, DMSO-d6, δ, ppm/32.1, —$\underline{C}$H$_2$—/115.4, 115.6, 128.8, 129.1, 131.4, 132.3, 155.7, 157.1, -Phenyl/125.2, 125.3, 125.8, 127.5, 129.7, 130.2, 131.4, 132.8, 136.6, -Anthryl). FIG. 2 shows a $^1$H-NMR chart, and FIG. 3 shows a $^{13}$C-NMR chart. In addition, blue luminescence was visually observed upon irradiation with a UV lamp (365 nm). FIG. 4 shows an absorption spectrum, and FIG. 5 shows a fluorescent spectrum (excitation wavelength: 380 nm).

Example 2

Figure 6:
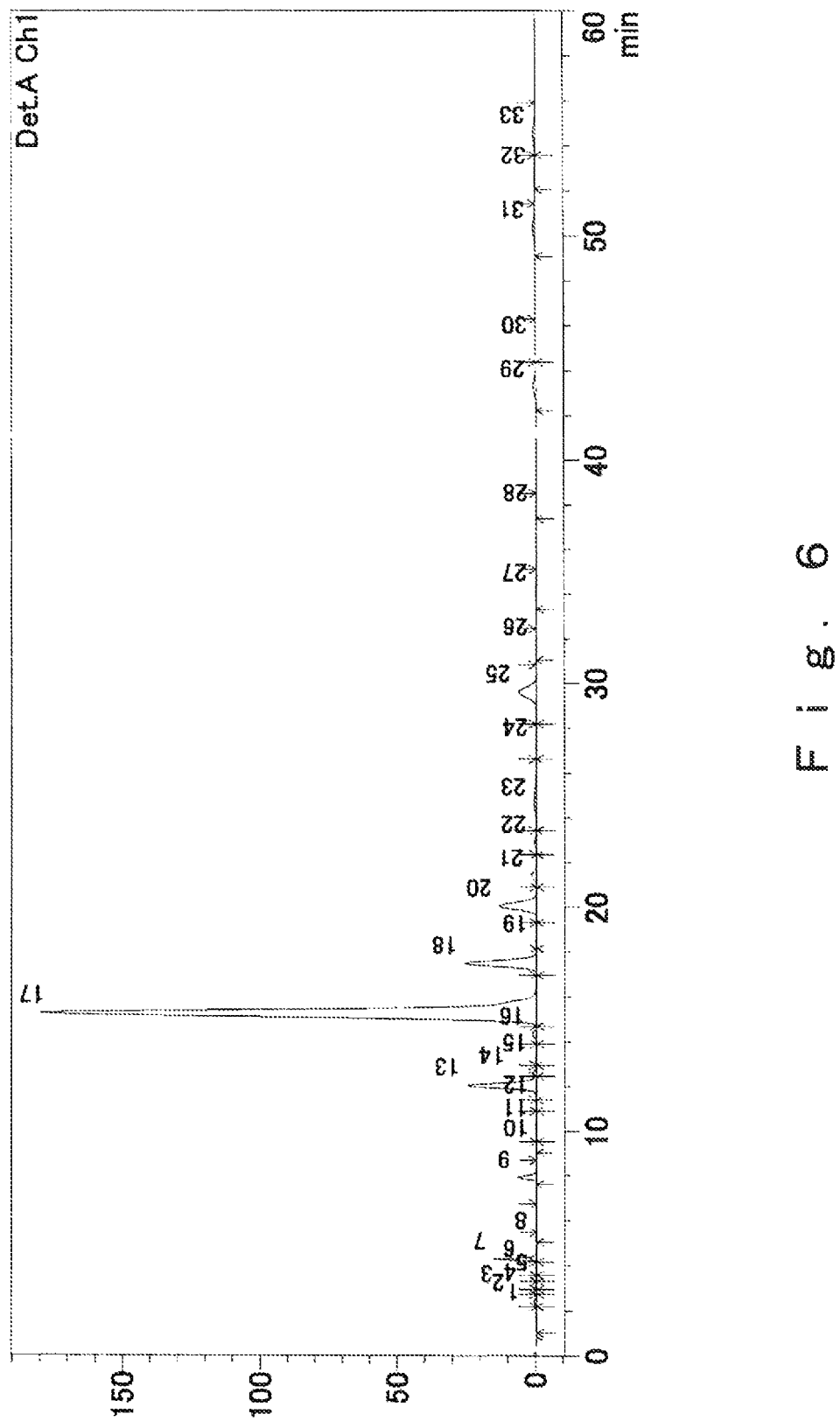
FIG. 6 shows a view illustrating an HPLC chart obtained after completing the reaction of Example 2.

An operation similar to Example 1 was carried out except that methanol was changed to ethylene glycol (11.3 g) in Example 1, whereby 49.9 g of pale yellow crystal (yield: 55.0%) was obtained. An HPLC chart obtained after completing the reaction is shown in FIG. 6.

The crystal obtained had a purity on GPC of 100%, a purity on HPLC of 99.5% and a melting point of 238° C., and blue luminescence was visually observed upon irradiation with a UV lamp (365 nm).

Example 3

An operation similar to Example 1 was carried out except that phenol was changed to 172.8 g of 2-naphthol (1.20 mol) and methanol was changed to ethylene glycol monomethyl ether, whereby 57.1 g of pale yellow crystal (yield: 50.0%) was obtained.

Figure 7:
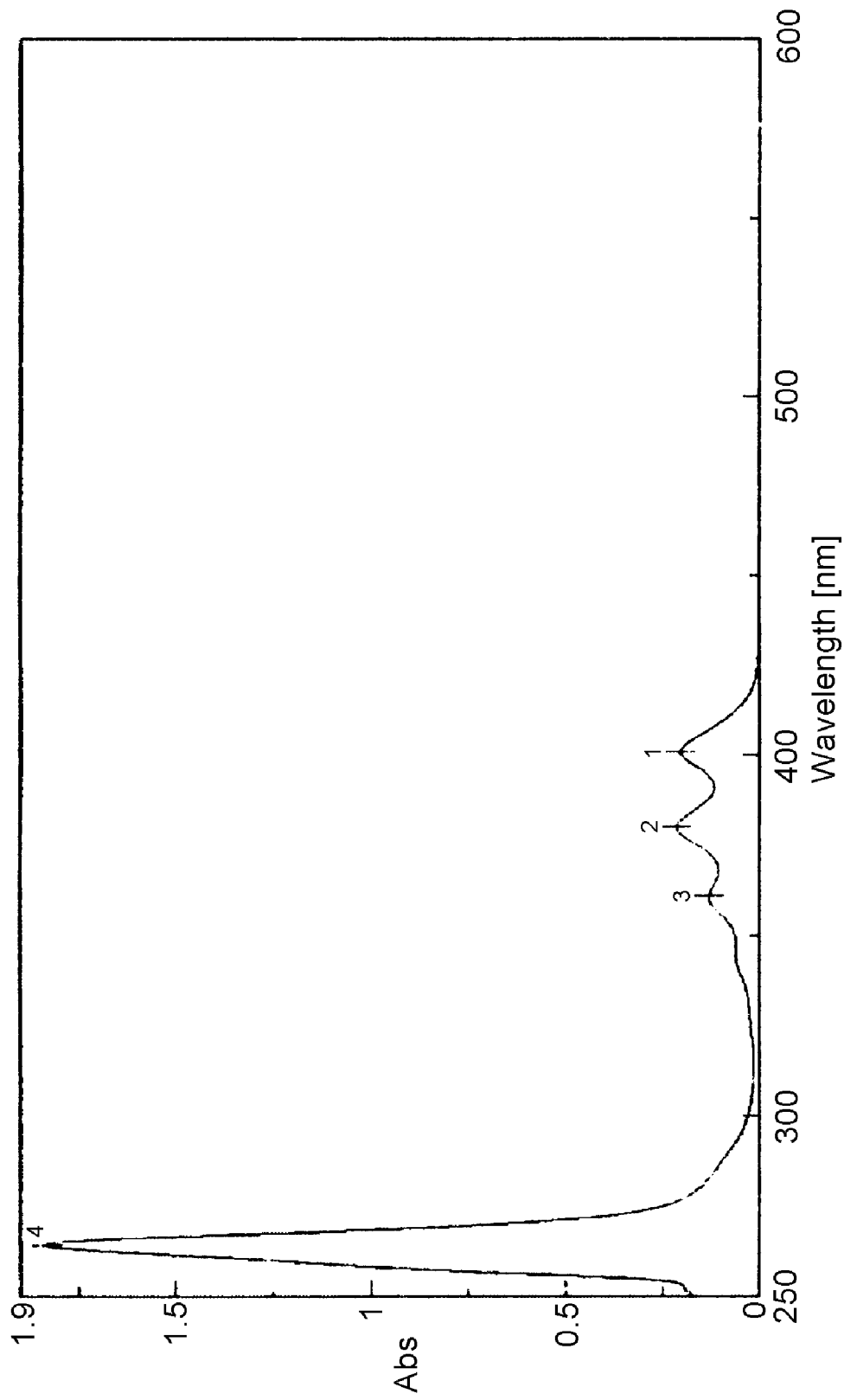
FIG. 7 shows a view illustrating an absorption spectrum of the intended product of Example 3.
Figure 8:
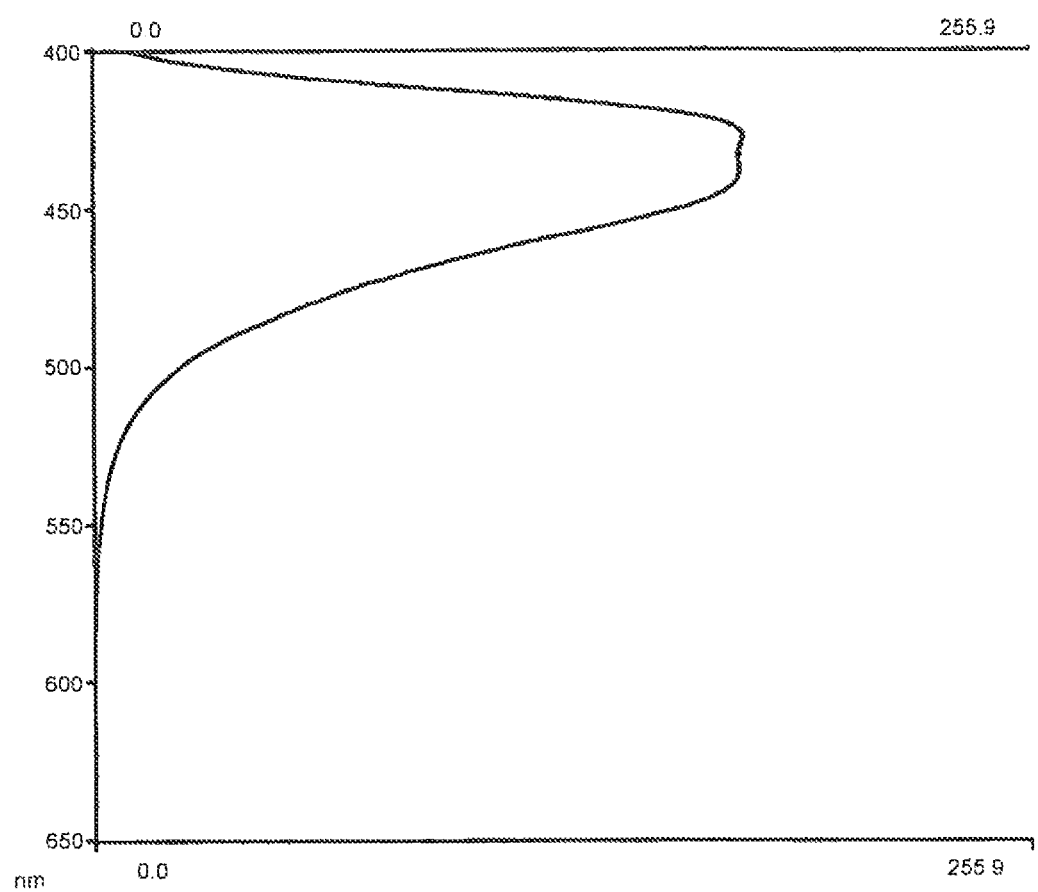
FIG. 8 shows a view illustrating a fluorescent spectrum of the intended product of Example 3.

The crystal obtained had a purity on GPC of 96.7%, a purity on HPLC of 99.4%, a melting point of 221° C. and a converted refractive index of 1.665 (25° C.), and ascertained to be 9-{(2-hydroxy-1-naphthyl)methyl}-10-(2-hydroxy-1-naphthyl)anthracene by way of $^1$H-NMR (400 MHz, DMSO-d6, δ, ppm/5.0, 2H, —C$\underline{H_2}$—/6.6, 6.8, 6.95, 7.05, 7.1, 7.2, 7.3, 12H, Naphtyl-$\underline{H}$/7.4, 7.5, 7.7, 8.4, 8H, Anthryl-$\underline{H}$/9.1, 9.7, 2H, —O$\underline{H}$). In addition, blue luminescence was visually observed upon irradiation with a UV lamp (365 nm). FIG. 7 shows an absorption spectrum, and FIG. 8 shows a fluorescent spectrum (excitation wavelength: 380 nm).

Example 4

Synthesis of Compound Using an Anthracene Derivative as an Intermediate Basic Material In a 1 L reaction vessel equipped with a reflux tube were charged 56.4 g of the crystal obtained in a similar manner to Example 1 (0.15 mol), 56.4 g of methanol and 222.0 g of epichlorohydrin (2.4 mol), and dissolution was permitted at 60° C. Thereto was added 25.0 g of 48% sodium hydroxide (0.30 mol) dropwise over 30 min with a dropping funnel, and the reaction was allowed at 60° C. for 9 hrs. Subsequently, the product was washed with 114 g of pure water four times, followed by concentration of the organic layer under a reduced pressure to obtain a resinous intended substance. The resinous matter cooled by allowing to stand still was crushed with a mortar, and stirred with 540 g of methanol to allow for precipitation of a crystal. Filtration and drying gave 67.7 g of a pale yellow.

Figure 9:
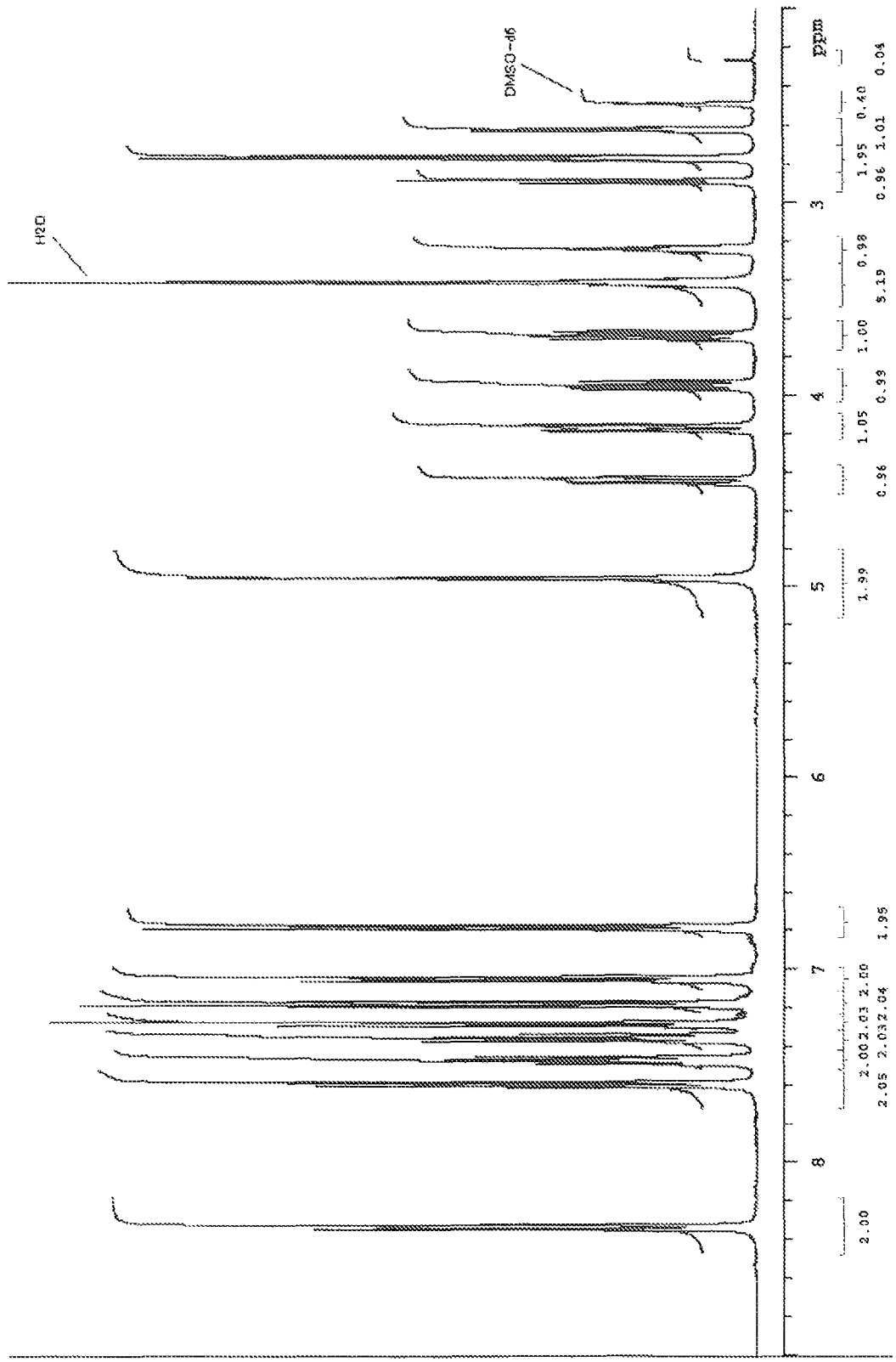
FIG. 9 shows a view illustrating a $^1$H-NMR chart of the intended product of Example 4.
Figure 10:
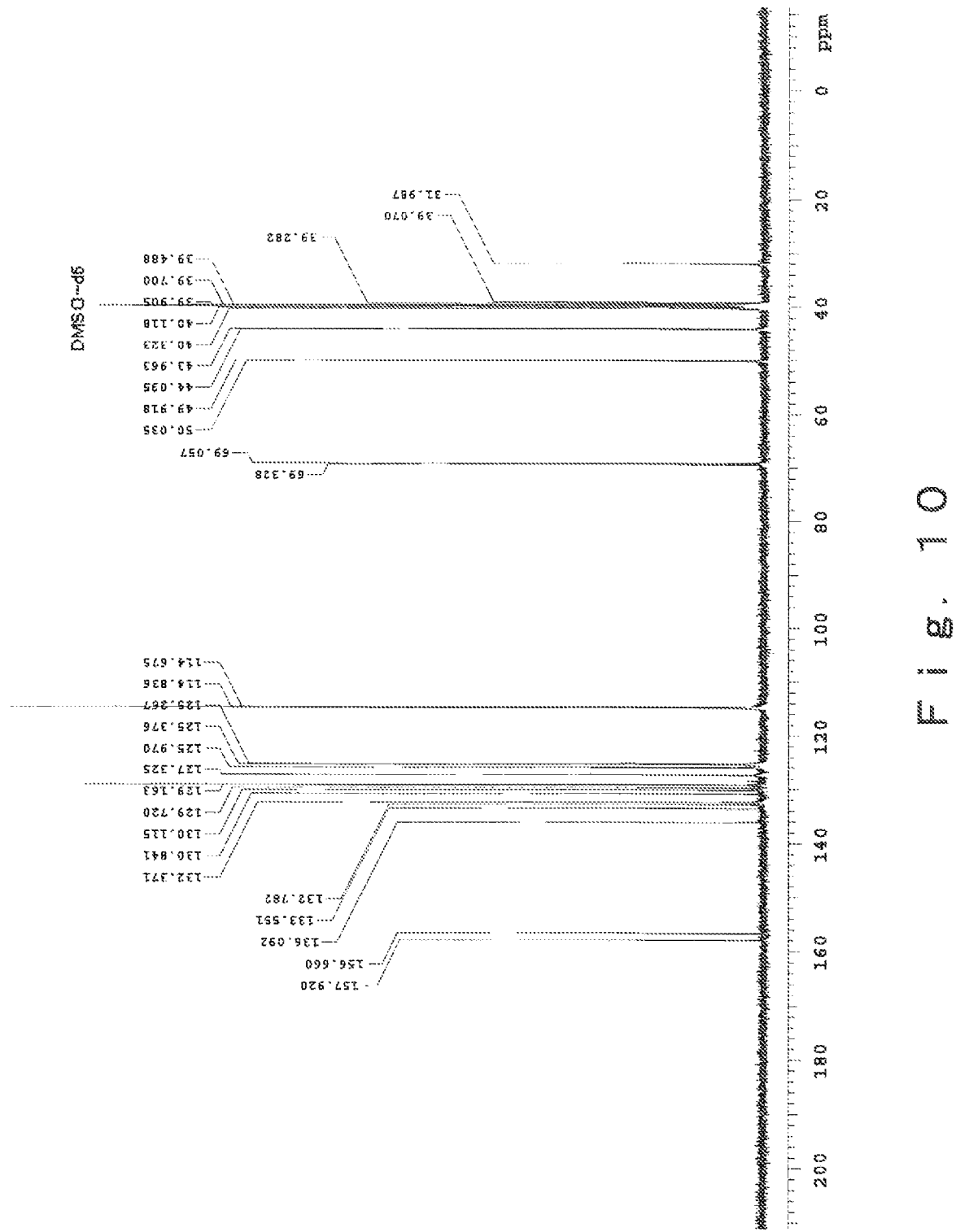
FIG. 10 shows a view illustrating a $^{13}$C-NMR chart of the intended product of Example 4.
Figure 11:
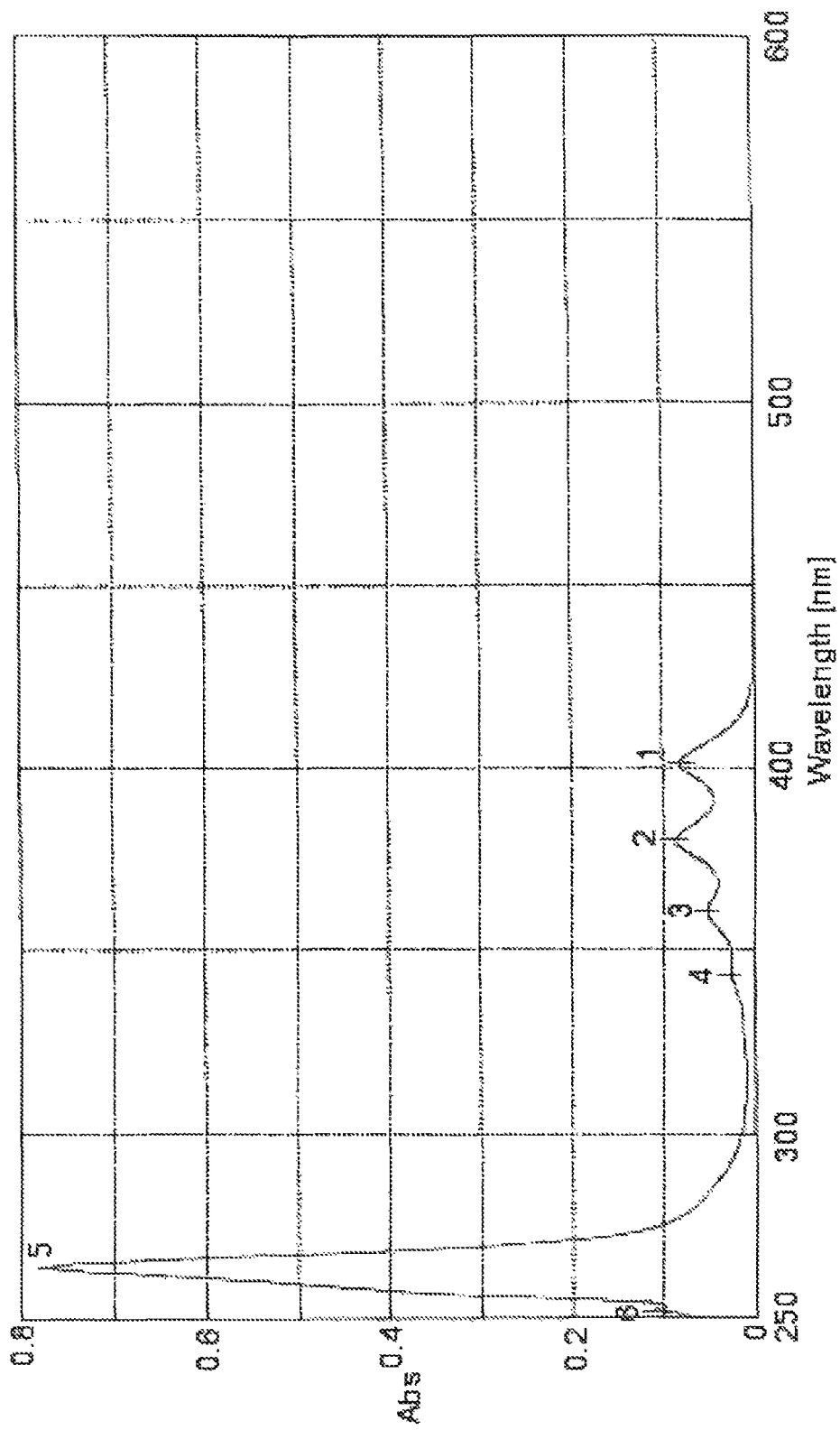
FIG. 11 shows a view illustrating an absorption spectrum of the intended product of Example 4.
Figure 12:
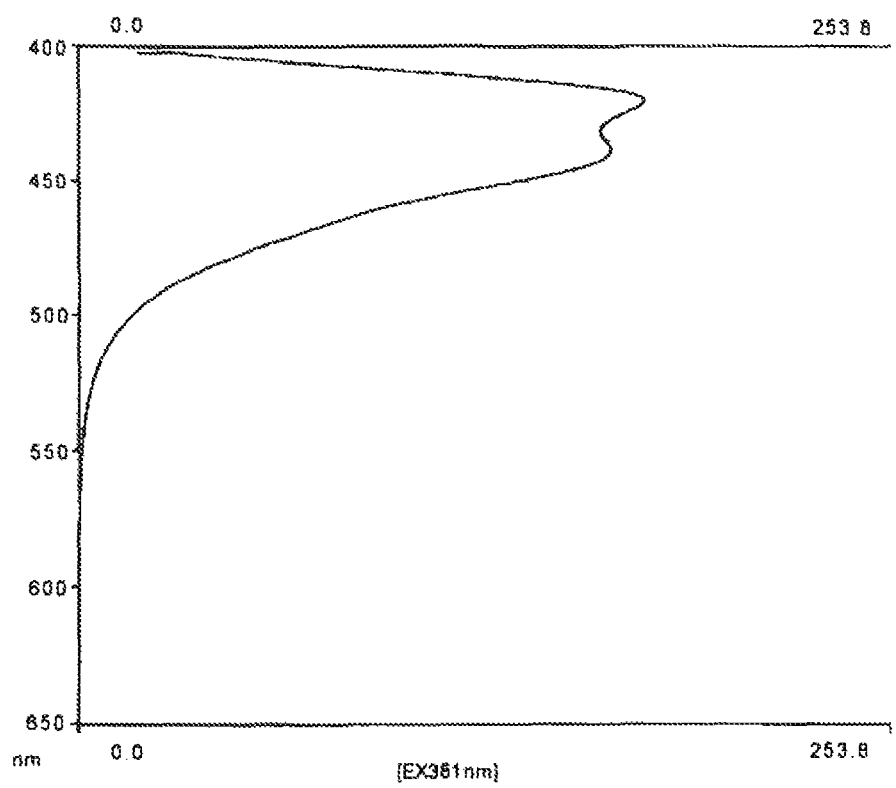
FIG. 12 shows a view illustrating a fluorescent spectrum of the intended product of Example 4.

The crystal obtained had a purity on GPC of 94.3%, a purity on HPLC of 99.0%, a melting point of 155° C., a converted refractive index of 1.653 (25° C.) and an epoxy equivalent of 248, and ascertained to be 9-(4-hydroxybenzyl)-10-(4-hydroxyphenyl)anthracene diglycidyl ether by way of $^1$H-NMR (400 MHz, DMSO-d6, δ, ppm/2.6, 2.76, 2.78, 2.9, 3.2, 3.4, 6H, Oxirane-H/3.7, 4.0, 4.2, 4.4, 4H, —O—CH$_2$-Oxirane/5.0, 2H, —CH$_2$—/6.8, 7.1, 7.2, 7.3, 8H, Phenyl-H/7.4, 7.5, 7.6, 8.3, 8H, Anthryl-H) and $^{13}$C-NMR (400 MHz, DMSO-d6, δ, ppm/32.0, —CH$_2$—/44.0, 44.1, 49.9, 50.0, Oxirane-C/69.1, 69.3, —O—CH$_2$-Oxirane/114.7, 114.8, 129.2, 129.7, 132.4, 132.8, 156.7, 157.9, -Phenyl/125.3, 125.4, 126.0, 127.3, 130.1, 130.8, 133.6, 136.1, -Anthryl). FIG. 9 shows a $^1$H-NMR chart, and FIG. 10 shows a $^{13}$C-NMR chart. In addition, blue luminescence was visually observed upon irradiation with a UV lamp (365 nm). FIG. 11 shows an absorption spectrum, and FIG. 12 shows a fluorescent spectrum (excitation wavelength: 381 nm).

Example 5

Preparation of Composition and Formation of Cured Product

The crystal obtained in Example 4 in an amount of 20.0 g, and methylhexahydrophthalic anhydride in amount of 12.2 gas a curing agent were weighed, and these were subjected to melt mixing on a hot plate at 180° C. Furthermore, 0.1 g of 1-(2-cyanoethyl)-2-ethyl-4-methylimidazole was added thereto as a curing accelerator, and the mixture was sufficiently stirred and degassed to obtain a composition.

The composition prepared as described above was poured into a die, and deaerated at 100° C. for 45 min under vacuum. Thereafter, curing was permitted at 100° C. for 3 hrs and then at 150° C. for 5 hrs while subjecting to compression at from ordinary pressure to 0.01 kgf/cm$^2$, followed by postcuring at 220° C. for 3 hrs to obtain a cured product.

The resulting cured product was cut into a size for each of various types of measuring methods, and evaluation of the characteristics was made, revealing a glass transition temperature of 211° C., a linear expansion coefficient of 93 ppm/° C., a water absorbing rate of 0.55%, and a residual carbon ratio of 12.74%.

Comparative Example 1

Figure 13:
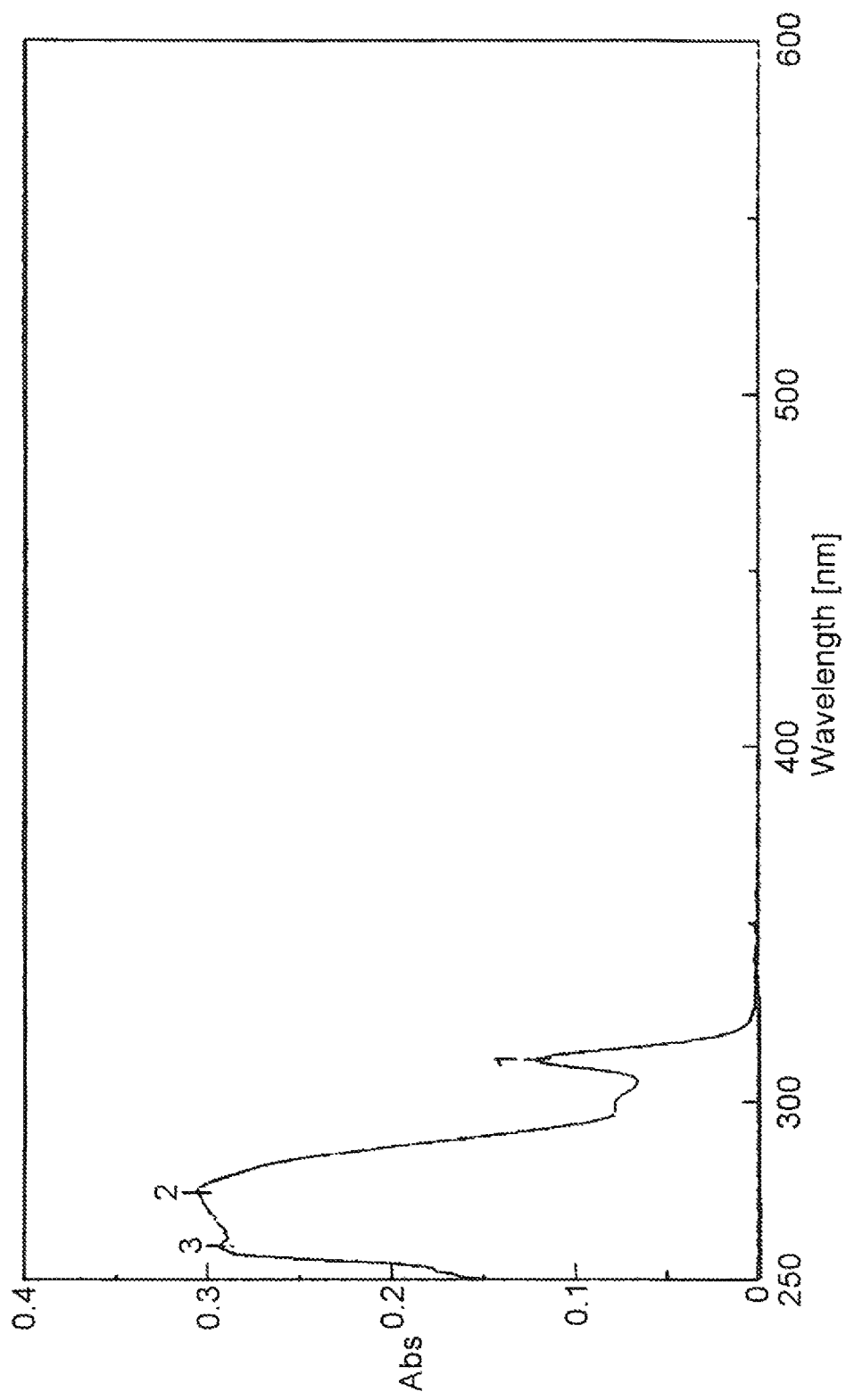
FIG. 13 shows a view illustrating an absorption spectrum of the compound of Comparative Example 1.
Figure 14:
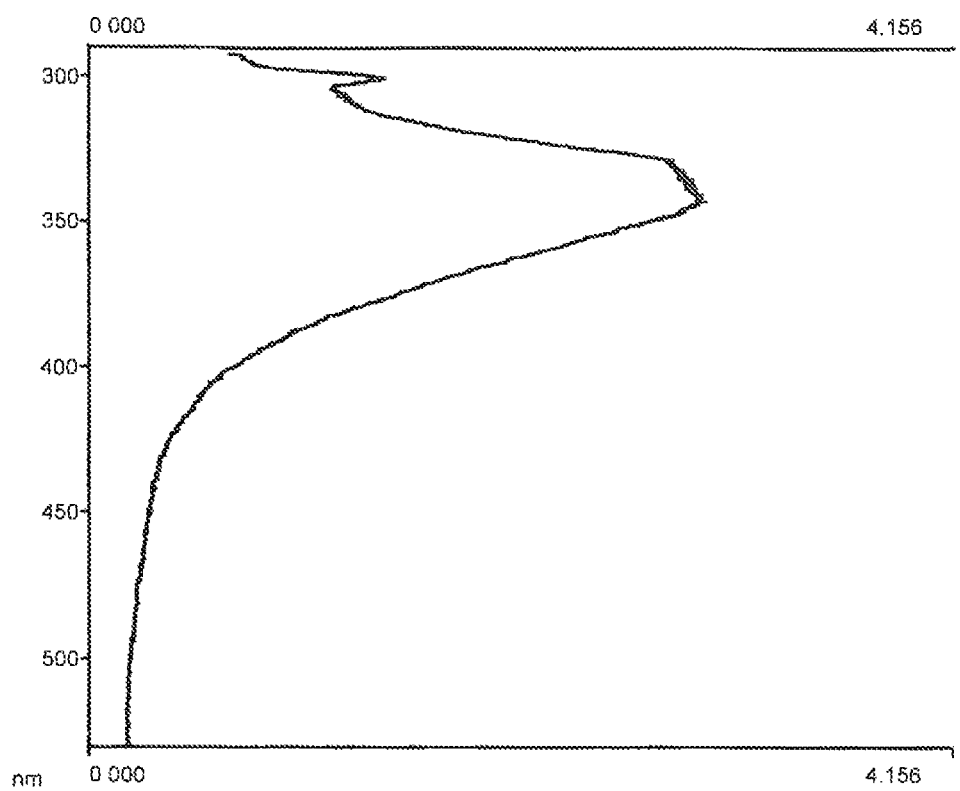
FIG. 14 shows a view illustrating a fluorescent spectrum of the compound of Comparative Example 1.

BPAF (trade name: manufactured by JFE Chemical Corporation; 9,9-bis(4-hydroxyphenyl)fluorine) that is a commercially available product of bisphenolfluorene was analyzed, and compared with bisphenolanthracene of Example 1, and with bisnaphtholanthracene of Example 2, revealing a purity on HPLC of 98.6%, a melting point of 223° C., and a converted refractive index of 1.664 (25° C.). Although irradiated with a UV lamp (365 nm), luminescence was not visual observed, and fluorescence intensity as determined by a fluorescent spectrophotometer was also very faint. FIG. 13 shows an absorption spectrum, and FIG. 14 shows a fluorescent spectrum (excitation wavelength: 275 nm).

Comparative Example 2

Figure 15:
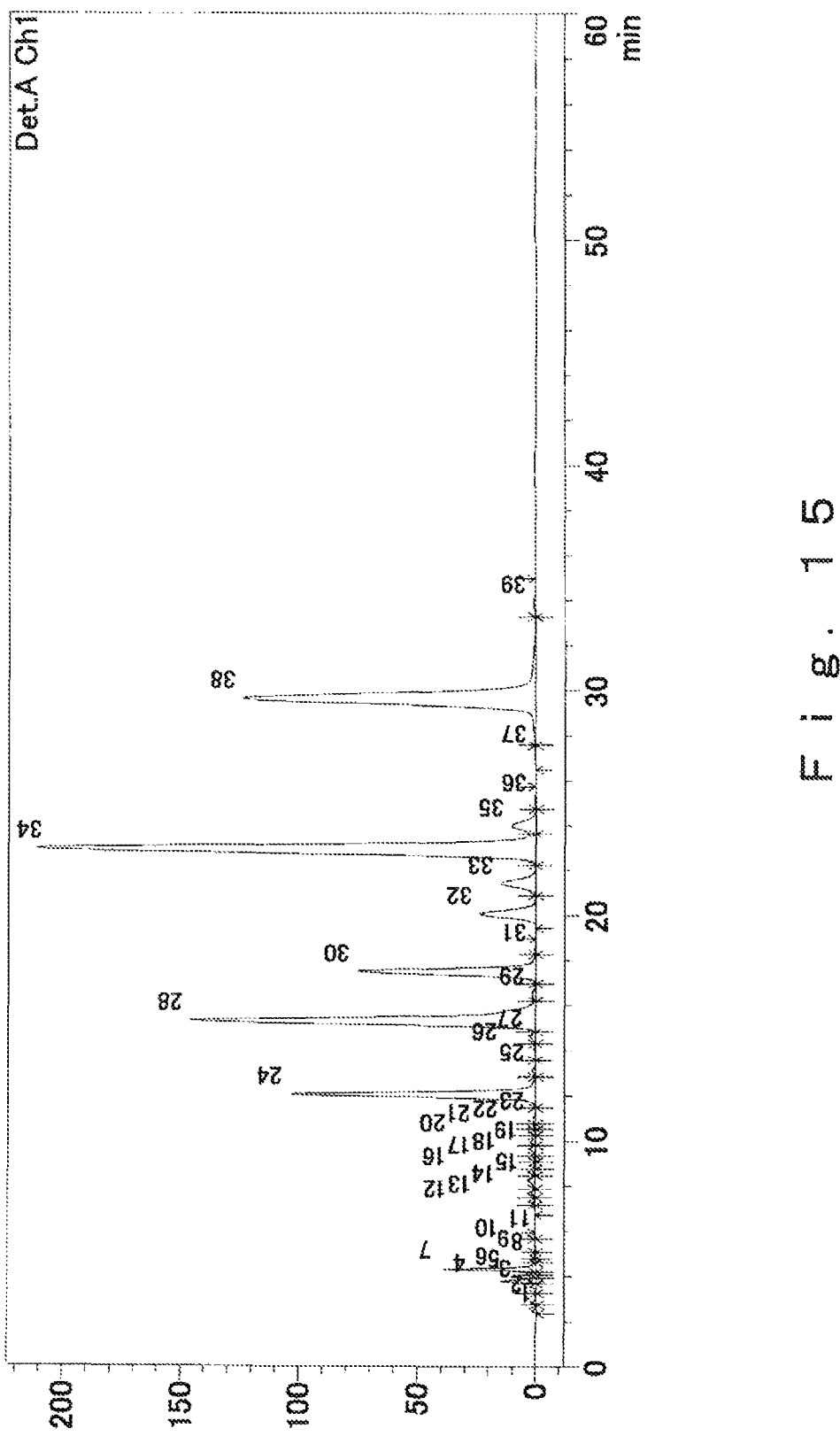
FIG. 15 shows a view illustrating an HPLC chart obtained after completing the reaction of Comparative Example 2.

An operation similar to Example 1 was carried out except that methanol was changed to toluene (11.3 g) in Example 1. HPLC determination carried out when the reaction was terminated confirmed that there were a large quantity of by-products other than the intended substance. The HPLC chart is shown in FIG. 15. In an attempt to remove a crystal in a subsequent method similar to that in Example 1, crystallization did not successfully occur.

Comparative Example 3

Figure 16:
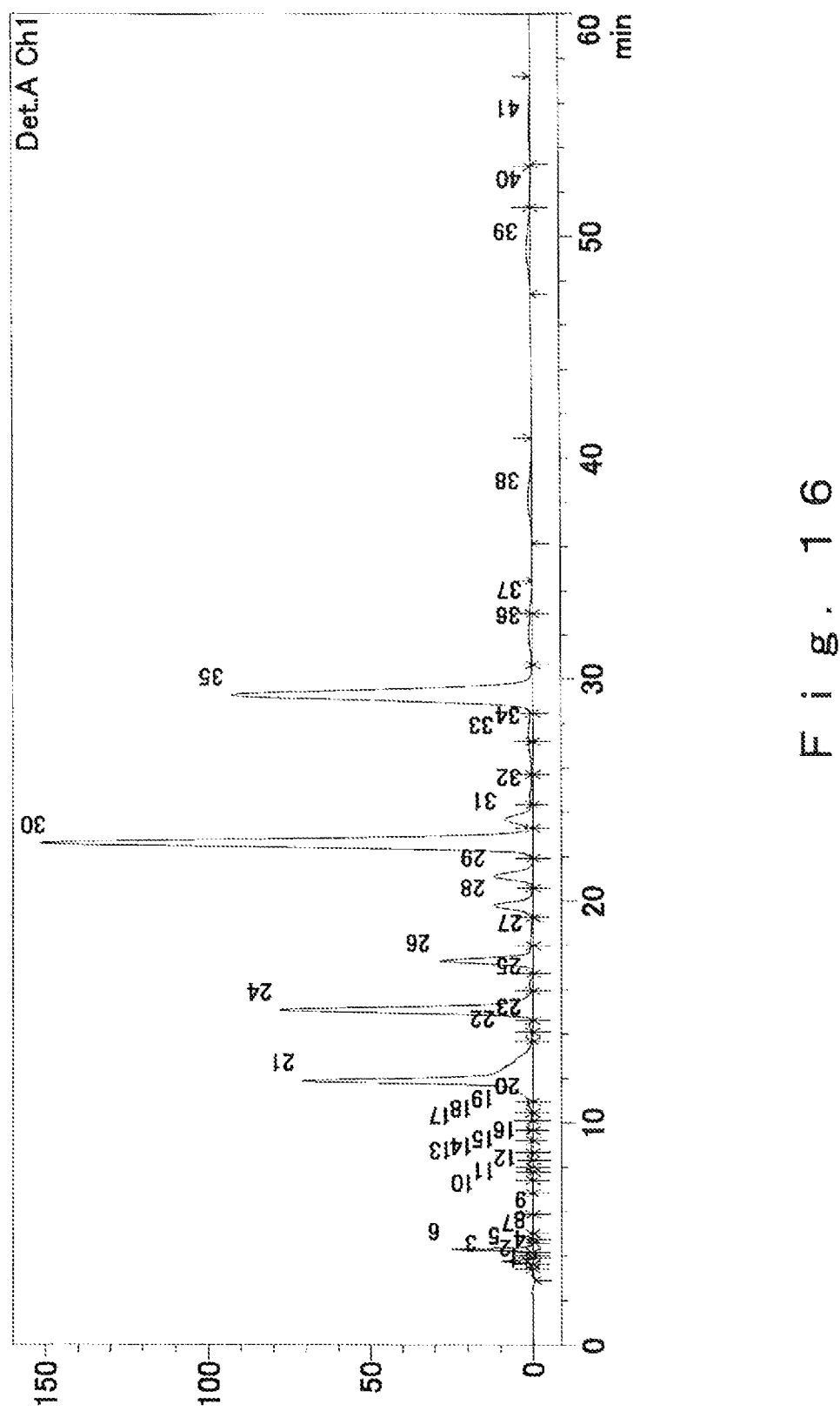
FIG. 16 shows a view illustrating an HPLC chart obtained after completing the reaction of Comparative Example 3.

An operation similar to Example 1 was carried out except that methanol was changed to cyclohexane (11.3 g) in Example 1. HPLC determination carried out when the reaction was terminated confirmed that there were a large quantity of by-products other than the intended substance. The HPLC chart is shown in FIG. 16. In an attempt to remove a crystal in a subsequent method similar to that in Example 1, crystallization did not successfully occur.

As shown in EXAMPLES, it was revealed that the anthracene derivatives according to the present invention synthesized in Example 1 to Example 3 had a melting point higher than the melting point of anthracene (218° C.), and a refractive index comparative to or higher than that of anthracene, while having fluorescence for ultraviolet rays comparative to anthracene. In addition, comparison of the anthracene derivative of Example 1 with bisphenolfluorene similarly having a bisphenol structure (Comparative Example 1) indicated to have a higher melting point and refractive index. Furthermore, production of the anthracene derivative suggested that it can be efficiently synthesized in an oxygen-containing inert organic solvent.

In addition, it was indicated that the compound of Example 4 obtained using the anthracene derivative according to the present invention synthesized in Example 1 as an intermediate basic material also had properties peculiar to anthracene such as fluorescent characteristics. Furthermore, it was indicated that the compound of Example 4 was also excellent in the reactivity, and the cured product of Example 5 obtained from a composition containing this compound had superior properties such as superior heat resistance, superior flame retardance, superior dimension accuracy and superior moisture resistance.

INDUSTRIAL APPLICABILITY

The anthracene derivative of the present invention and the compound obtained using the same as an intermediate can provide a highly versatile material that imparts various characteristics such as high carbon density, high melting point, high refractive index, and fluorescent properties, and can be used for, e.g., basic materials of resins such as basic materials of epoxy resins, basic materials of polycarbonate resins and basic materials of acrylic resins. These resin and the like produced using the anthracene derivative as a basic material can be used for, e.g., laminating materials, coating materials such as paints, optical materials such as lenses and optical sheets, recording materials such as hologram recording materials, advanced functional materials such as organic photo conductors, photoresist materials, antireflection films and semiconductor sealing materials, magnetic materials such as magnetic molecular memory, and the like, and these can be used as, for example, materials for organic solar cells, organic EL devices, liquid crystal display devices and the like. In addition, the anthracene derivative of the present invention can be used for not only basic materials of resins but also, for example, intermediates of medical drugs and intermediates of dyes.

The invention claimed is:

1. An anthracene derivative represented by the following general formula (1):

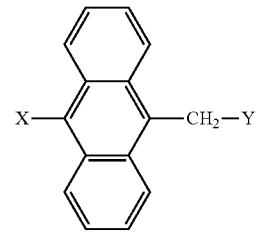

in the formula (1), X and Y each independently represent a hydroxyaryl group.

2. The anthracene derivative according to claim 1, wherein X and Y represent a hydroxyphenyl group.

3. A compound obtained by subjecting the anthracene derivative according to claim 1 to allylation, glycidylation, acrylation, methylolation or benzooxazination.

4. A composition comprising: the anthracene derivative according to claim 1 or the compound according to claim 3; and optionally a least one selected from the group consisting of a solvent, an inorganic filler, a pigment, a thixotropifying agent, a flow performance improver, a curing agent, and a curing accelerator.

5. A cured product obtained by a process comprising irradiating with light or heating the composition according to claim 4 to be cured.

6. A process for producing an anthracene derivative represented by the following general formula (1):

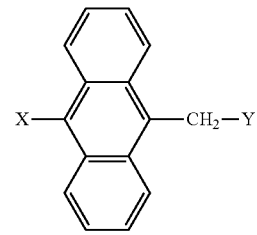

in the formula (1), X and Y each independently represent a hydroxyaryl group, the process comprising allowing at least one compound selected from phenols to react with anthracene-9-carboaldehyde in the presence of an oxygen-containing inert organic solvent and an acid catalyst.

7. The process for producing an anthracene derivative according to claim 6, wherein the at least one compound selected from phenols is phenol.

* * * * *